(12) United States Patent
Wang et al.

(10) Patent No.: US 9,156,189 B2
(45) Date of Patent: Oct. 13, 2015

(54) SYSTEMS AND METHODS FOR HIGH-THROUGHPUT MICROFLUIDIC BEAD PRODUCTION

(75) Inventors: Tza-Huei Wang, Timonium, MD (US); Weijie Beh, Baltimore, MD (US); Dara L. Kraitchman, Oxford, MD (US); Hsa-Quan Mao, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 43 days.

(21) Appl. No.: 13/822,983

(22) PCT Filed: Oct. 3, 2011

(86) PCT No.: PCT/US2011/054598
§ 371 (c)(1),
(2), (4) Date: Mar. 13, 2013

(87) PCT Pub. No.: WO2012/047802
PCT Pub. Date: Apr. 12, 2012

(65) Prior Publication Data
US 2013/0183246 A1     Jul. 18, 2013

Related U.S. Application Data

(60) Provisional application No. 61/388,790, filed on Oct. 1, 2010.

(51) Int. Cl.
*A61B 5/055* (2006.01)
*B29B 9/12* (2006.01)
*B01J 13/00* (2006.01)
*A61K 9/16* (2006.01)

(52) U.S. Cl.
CPC ............... *B29B 9/12* (2013.01); *B01J 13/0052* (2013.01); *A61K 9/16* (2013.01)

(58) Field of Classification Search
USPC ......................................................... 424/9.3
See application file for complete search history.

(56) References Cited

U.S. PATENT DOCUMENTS

| 2004/0062681 | A1 | 4/2004 | Winston |
| 2006/0051329 | A1* | 3/2006 | Lee et al. ............... 424/93.7 |
| 2006/0134152 | A1 | 6/2006 | Prouzet et al. |

FOREIGN PATENT DOCUMENTS

| EP | 0760239 A2 | 3/1997 |
| KR | 10-0523953 B1 | 10/2005 |
| KR | 10-2007-0084325 A | 8/2007 |
| WO | WO-03094930 A1 | 11/2003 |
| WO | WO2005120589 * | 12/2005 ............. A61K 51/06 |

OTHER PUBLICATIONS

Barnett et al., Synthesis of magnetic resonance-, X-ray- and ultrasound-visible alginate microcapsules for immunoisolation and noninvasive imaging of cellular therapeutics, Nature Protocols vol. 6 No. 8 Jul. 2011: 1142-1151.
Dohnal et al., Inkjet fabrication and characterization of calcium alginate microcapsules. Powder Technology, Powder Technology, 2009 254-259.
Haeberle et al., Alginate bead fabrication and encapsulation of living cells under centrifugally induced artificial gravity conditions, Journal of Microencapsulation, Jun. 2008; 25(4): 267-274.
Kim et al., Rapid exchange of oil-phase in microencapsulation chip to enhance cell viability, Lab Chip, 2009, 9, 1294-1297.
Quake et al., From micro- to nanofabrication with soft materials, Science, Nov. 24, 2000;290(5496):1536-1540.
Zhao et al., Generation of Janus alginate hydrogel particles with magnetic anisotropy for cell encapsulation, Lab Chip, Oct. 21, 2009; 9(20):2981-2986.

* cited by examiner

*Primary Examiner* — Michael G Hartley
*Assistant Examiner* — Melissa Perreira
(74) *Attorney, Agent, or Firm* — Venable LLP; Henry J. Daley; Miguel A. Lopez

(57) ABSTRACT

A system for producing microbeads includes a microfluidic device defining a supply channel and a shearing channel, a microbead precursor material disposed in the supply channel, a carrier fluid disposed in the shearing channel, and a pressure distribution system fluidly connected to each of the supply channel and the shearing channel to control at least relative pressures of the microbead precursor material and the carrier fluid. The supply channel includes a check valve adapted to be subjected to a bias pressure that is sufficient to close the check valve to flow of microbead precursor material when a supply pressure of the microbead precursor material is below a threshold pressure and is open to flow of the microbead precursor material when the supply pressure of the microbead precursor material is greater than the threshold pressure. An end of the supply channel opens into the shearing channel such that the microbead precursor material is sheared into droplets by the carrier fluid flowing through the shearing channel. A pressure of the carrier fluid is less than the bias pressure. The microbead precursor material and the carrier fluid are substantially immiscible.

17 Claims, 8 Drawing Sheets

SYSTEMS AND METHODS FOR HIGH-THROUGHPUT MICROFLUIDIC BEAD PRODUCTION

CROSS-REFERENCE OF RELATED APPLICATION

This application claims priority to U.S. Provisional Application No. 61/388,790 filed Oct. 1, 2010, the entire contents of which are hereby incorporated by reference, and is a U.S. national stage application under 35 U.S.C. §371 of PCT/US2011/05498, filed Oct. 3, 2011, the entire contents of which are incorporated herein by reference.

This invention was made with Government support of Grant No. R21/R33 HL89029, awarded by the Department of Health and Human Services, The National Institutes of Health (NIH); and Grant No. 90028869, awarded by DARPA. The U.S. Government has certain rights in this invention.

BACKGROUND

1. Field of Invention

The field of the currently claimed embodiments of this invention relates to systems and methods for high-throughput production of microbeads.

2. Discussion of Related Art

Microencapsulation is an attractive way to deliver cells and biologics into the human body, providing immunoisolation while allowing biomolecules, either preloaded or synthesized in situ by cells, to be released in a controlled manner. Typical microencapsulation involves injecting alginate from a syringe into a bath of calcium solution. While the generation process is rapid, the size distribution is extremely polydisperse. In addition, gel beads smaller than 300 microns cannot be routinely made, making injection through small bore catheters almost impossible. There remains a need for systems and methods to generate uniform microbeads that are small (<100 μm) at quantities that are suitable for clinical applications.

Reported microbead generation on microfluidic chips often involve fusion of manually-synchronized alginate and calcium droplets in oil, which severely limits the rate of bead generation (Zhao L B, Pan L, Zhang K, Guo SS, Liu W, Wang Y, et al. Generation of Janus alginate hydrogel particles with magnetic anisotropy for cell encapsulation. Lab Chip 2009 Oct. 21;9(20):2981-2986). Generation frequencies range from single hertz to a theoretical maximum of 4 kHz for inkjet-based techniques, although in practice Dohnai et al. only achieved 30 Hz (Dohnal J, Stepánek F. Inkjet fabrication and characterization of calcium alginate microcapsules. Powder Technology;200(3):254-259). Centrifugation-based generation results in comparable frequency to our method at 600 Hz, but can only prepare beads with diameters of hundreds of microns (Haeberle S, Naegele L, Burger R, von Stetten F, Zengerle R, Ducree J. Alginate bead fabrication and encapsulation of living cells under centrifugally induced artificial gravity conditions. J Microencapsul 2008 Jun.;25(4):267-274). On the other hand, a recent report used oleic acid to act as both continuous phase (with alginate as the discrete phase) and calcium reservoir (Kim C, Lee K S, Kim Y E, Lee K J, Lee S H, Kim TS, et al. Rapid exchange of oil-phase in microencapsulation chip to enhance cell viability. Lab Chip 2009 May 7;9(9):1294-1297). Although it solved the problem of synchronizing the different aqueous inlets, clogging at the droplet generation nozzle was a significant problem, especially at higher generation frequencies, where a delicate balance of flow pressures must be maintained.

Another challenge in high frequency generation is bead aggregation, since only partial crosslinking occurs at high generation frequency due to relatively low saturation concentration of calcium ions in the oil phase. There thus remains a need for improved systems and methods for producing microbeads.

SUMMARY

A system for producing microbeads according to an embodiment of the current invention includes a microfluidic device defining a supply channel and a shearing channel, a microbead precursor material disposed in the supply channel, a carrier fluid disposed in the shearing channel, and a pressure distribution system fluidly connected to each of the supply channel and the shearing channel to control at least relative pressures of the microbead precursor material and the carrier fluid. The supply channel includes a check valve adapted to be subjected to a bias pressure that is sufficient to close the check valve to flow of microbead precursor material when a supply pressure of the microbead precursor material is below a threshold pressure and is open to flow of the microbead precursor material when the supply pressure of the microbead precursor material is greater than the threshold pressure. An end of the supply channel opens into the shearing channel such that the microbead precursor material is sheared into droplets by the carrier fluid flowing through the shearing channel. A pressure of the carrier fluid is less than the bias pressure. The microbead precursor material and the carrier fluid are substantially immiscible.

A microfluidic device for the fabrication of microbeads according to an embodiment of the current invention includes a substrate, a first structured layer bonded to the substrate to define a channel layer of microfluidic channels, and a second structured layer bonded to the first structured layer to define a control layer of control channels. The channel layer includes a supply channel and a shearing channel that intercepts the supply channel. The supply channel is adapted to supply microbead material to be sheared into droplets for the formation of microbeads by a carrier fluid flowing through the shearing channel, and the supply channel includes a check valve adapted to prevent back flow of carrier fluid into the supply channel.

A method of producing microbeads according to an embodiment of the current invention includes providing a microfluidic device that has a supply channel and a shearing channel arrange such that the supply channel opens into the shearing channel, wherein the microfluidic device also has a check valve arranged along the supply channel; applying a bias pressure to the check valve such that the check valve is closed; applying a pressure to a carrier fluid in the shearing channel subsequent to the applying the bias pressure that is less than the bias pressure; applying a pressure to a microbead precursor material in the supply channel subsequent to the applying the pressure to the carrier fluid such that the microbead precursor material forces the check valve open; and collecting microbeads from an outlet of the microfluidic device.

A microbead precursor material according to an embodiment of the current invention includes alginate and a contrast agent.

A microbead according to an embodiment of the current invention includes alginate and a contrast agent.

BRIEF DESCRIPTION OF THE DRAWINGS

Further objectives and advantages will become apparent from a consideration of the description, drawings, and examples.

FIG. 7A (top left) shows that a large number of monodisperse beads can be generated and collected on-chip. FIG. 7B (bottom left) shows an example of barium sulfate (Ba) crystals (black) and gadopentetate dimeglumine (Gd) that are co-encapsulated in microbeads (circled). Monodispersity decreases slightly when barium sulfate is introduced due to disruption to flow streams, though beads remain smaller than 100 μm across the board (bars=100 μm). FIG. 7C (right) provides an example in which multiplanar reformats were obtained on standard reconstructed cone beam computed tomographic (CBCT) images. The Ba-Gd beads appear as a hyperintense pellet in the bottom of the microcentrifugation tubes on the CBCTs.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention are directed to systems and methods to generate monodisperse gel microbeads that are suitable for encapsulation of various compounds, including but not limited to cells, biological molecules, pharmaceuticals, radiotracers, imaging contrast agents and magnetic particles for therapeutic and other applications, at kilohertz frequencies on a single microfluidic device. A device according to an embodiment of the current invention utilizes calcium ion-alginate physical interactions to encapsulate multiple payloads into each microbead. The surface of these beads can also be coated with various molecules on-chip to achieve desirable physical and biological properties.

As used herein, the term "microbead" is intended to include beads that have average diameters of at least 2 μm and less than 1 mm. It is not required that the microbeads be spherical, or approximately spherical, although they can be according to some embodiments of the current invention.

Microencapsulation is an attractive way to deliver cells and biologics into the human body, providing immunoisolation while allowing biomolecules, either preloaded or synthesized in situ by cells, to be released in a controlled manner. Typical microencapsulation involves injecting alginate from a syringe into a bath of calcium solution. While the generation process is rapid, the size distribution is extremely polydisperse. In addition, gel beads smaller than 300 microns cannot be routinely made, thus requiring large bore needles or catheters for injection. Alternative methods are either too slow (microfluidic droplet generators), produce beads that are too polydisperse (centrifugal acceleration) or too irregular (inkjet-based piezoelectric elements). Also, incorporation of different payloads is often difficult. Finally, almost none of the existing methods provide an easy way to modify the surface of the beads without multiple tedious washing and incubation steps. Methods according to some embodiments of the current invention not only can address all these issues, but also can allow for extremely easy scaling up due to the robustness of the system.

Figure 1:
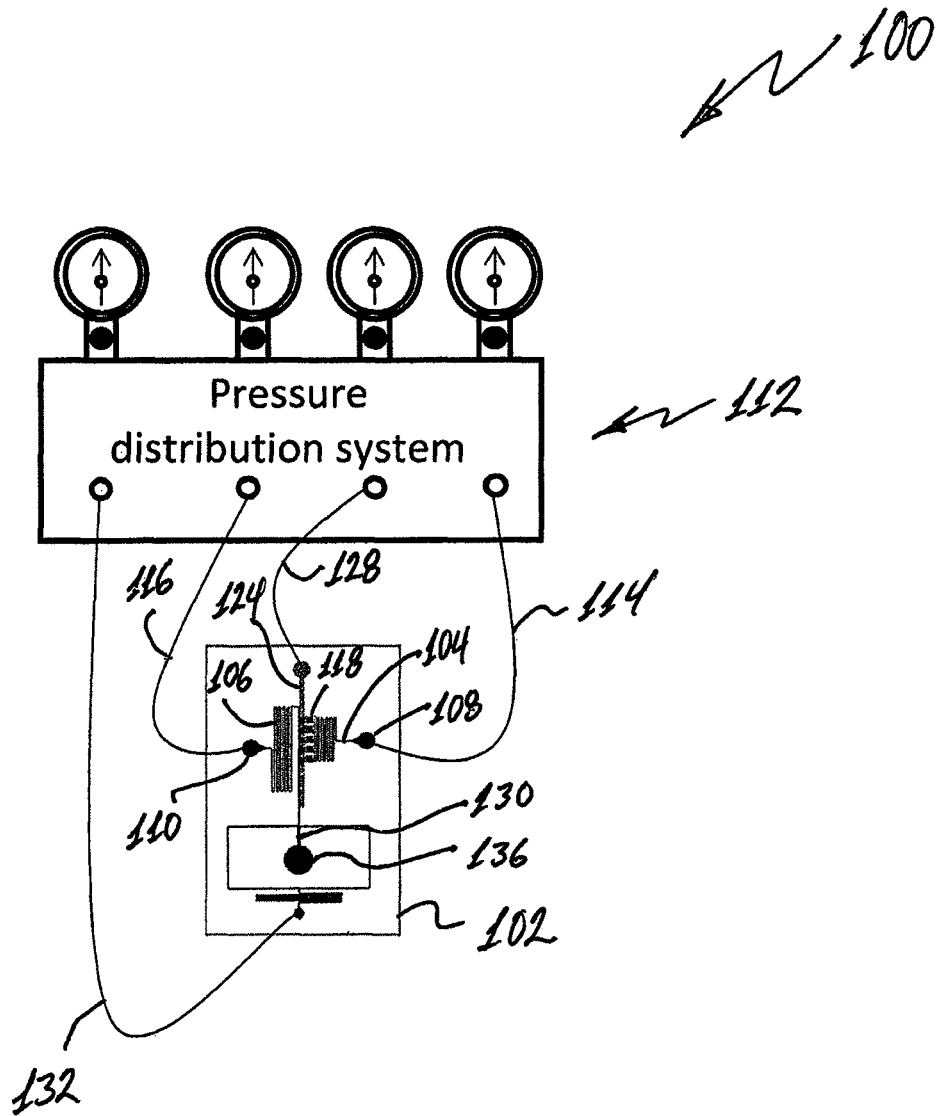
FIG. 1 is a schematic illustration of a system for producing microbeads according to an embodiment of the current invention.

FIG. 1 provides a schematic illustration of a system 100 for producing microbeads according to an embodiment of the current invention. The system 100 includes a microfluidic device 102 that defines a supply channel 104 and a shearing channel 106 therein. During production, there is a microbead precursor material disposed in the supply channel 104. Microfluidic device 102 can include a chamber 108, for example, for storing the microbead precursor material. During production, there is a carrier fluid disposed in the shearing channel 106. A chamber 110 can be included to store carrier fluid, for example.

The system 100 also includes a pressure distribution system 112 fluidly connected to each of the supply channel 104, for example by tube 114, and to the shearing channel 106, for example by tube 116, to control at least relative pressures of the microbead precursor material and the carrier fluid. The supply channel 104 includes a check valve 118 (see, also FIG. 2B) adapted to be subjected to a bias pressure that is sufficient to close the check valve 118 to flow of microbead precursor material when a supply pressure of the microbead precursor material is below a threshold pressure and is open to flow of the microbead precursor material when the supply pressure of the microbead precursor material is greater than the threshold pressure. An end 120 of the supply channel 104 opens into the shearing channel 106 such that the microbead precursor material is sheared into droplets (e.g., droplet 122) by the carrier fluid flowing through the shearing channel 106. During operation, a pressure of the carrier fluid is less than the bias pressure, and the microbead precursor material and the carrier fluid are substantially immiscible. FIG. 2A shows an embodiment of the device 102 in more detail, FIG. 2B is a close up schematic view show droplet formation, and FIG. 2C shows an actual example of droplet formation.

Figure 4:
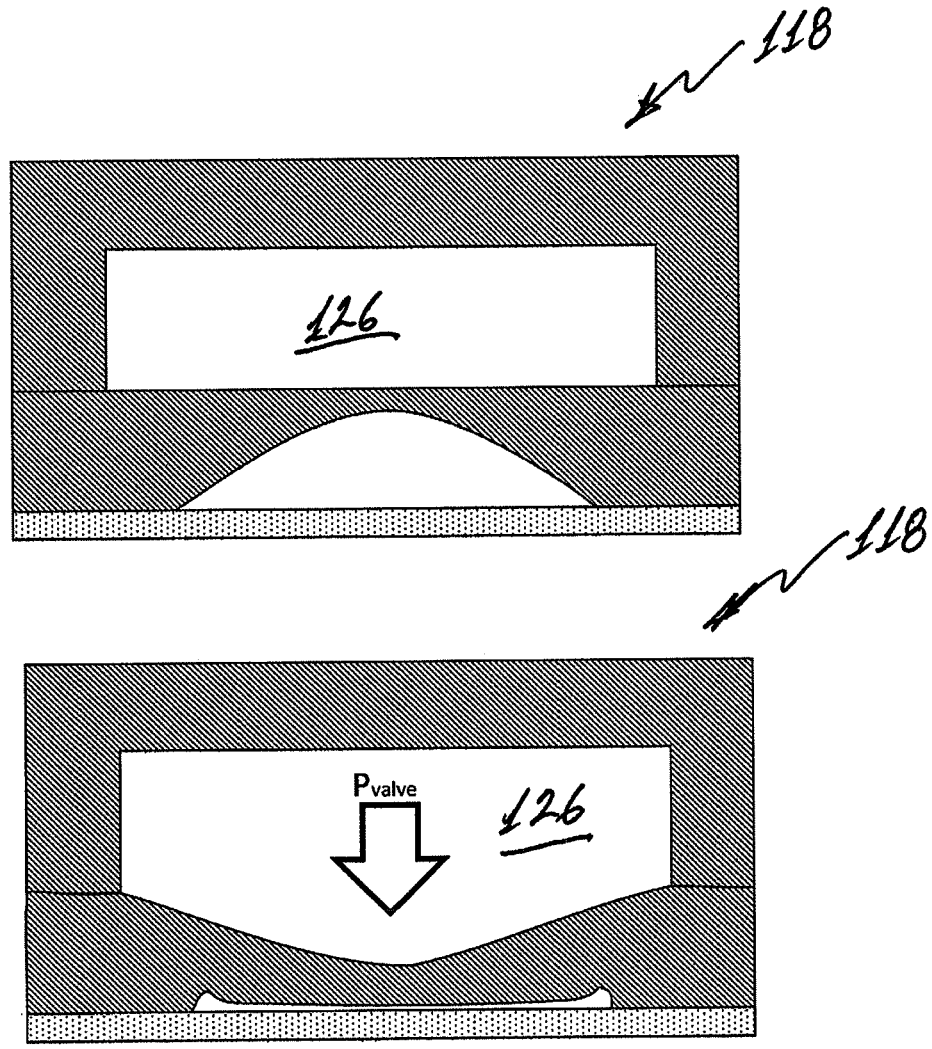
FIG. 4 is a cross sectional view of the check valve of the embodiment of FIG. 2A in an open configuration (top) and a closed configuration (bottom).

In some embodiments of the current invention, the bias pressure applied to the check valve 118 can be hydraulically or pneumatically applied. However, the general concepts of the current invention are not limited to these examples. For example, actuators or other mechanical means could be applied against the check valve in alternative embodiments. In some embodiments, the microfluidic device 102 further defines a control channel 124 operatively connected to the check valve 118 with a control fluid 126 disposed in the control channel 124 (see also FIG. 4). The pressure distribution system 112 is further fluidly connected to the control channel 124 to control the bias pressure. For example a tube 128 can fluidly connect the pressure distribution system 112 to the control channel 124.

The microfluidic device 102 can further define a stabilizing channel 130 that has a stabilizing fluid disposed therein. The stabilizing fluid can be at least partially miscible with the microbead precursor material and the carrier material. The stabilizing channel 130 is arranged such that the stabilizing fluid interfaces with the carrier fluid to further stabilize the droplets to form the microbeads. The stabilizing channel 130 can be fluidly connected to the pressure distribution system 112, for example by tube 132. In the example of FIG. 1, each of the supply channel 104, the shearing channel 106, the control channel 124 and the stabilizing channel 130 has a separate pressure regulator and pressure gauge. However, the concepts of the current invention are not limited to this particular example.

Figures 2A, 2B, 2C:
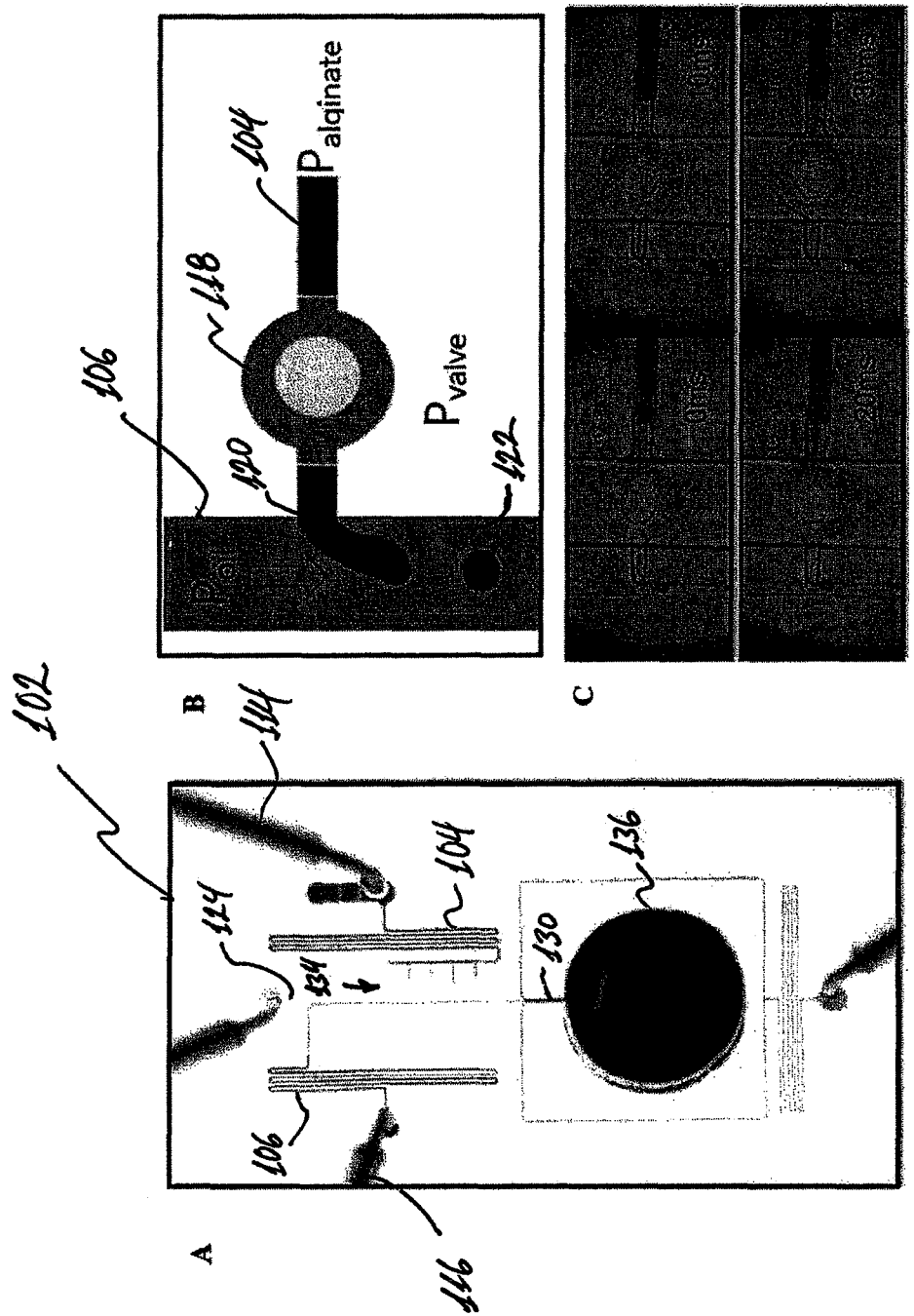
FIG. 2A is an example of a microfluidic device for producing microbeads according to an embodiment of the current invention.
FIG. 2B is a schematic illustration of the supply channel and check valve sections of the microfluidic device of FIG. 2A.
FIG. 2C shows an example of droplet formation for a time sequence using the microfluidic device of FIG. 2A.
Figure 3:
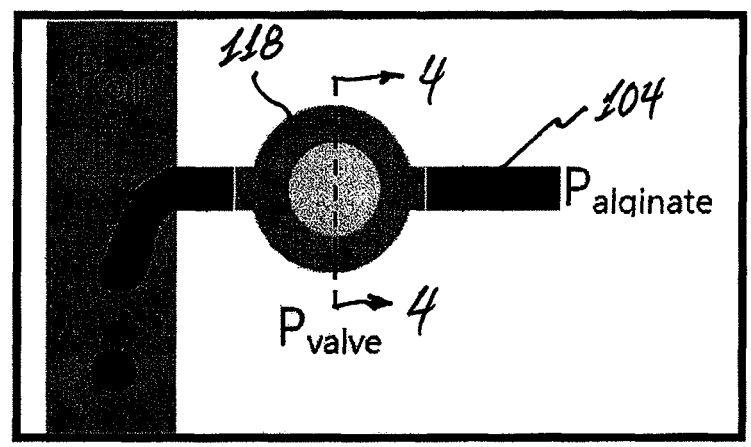
FIG. 3 is a schematic illustration of the supply channel and check valve sections of the microfluidic device of FIG. 2A also showing a cut line corresponding to the cross sectional view of FIG. 4.
Figure 5:
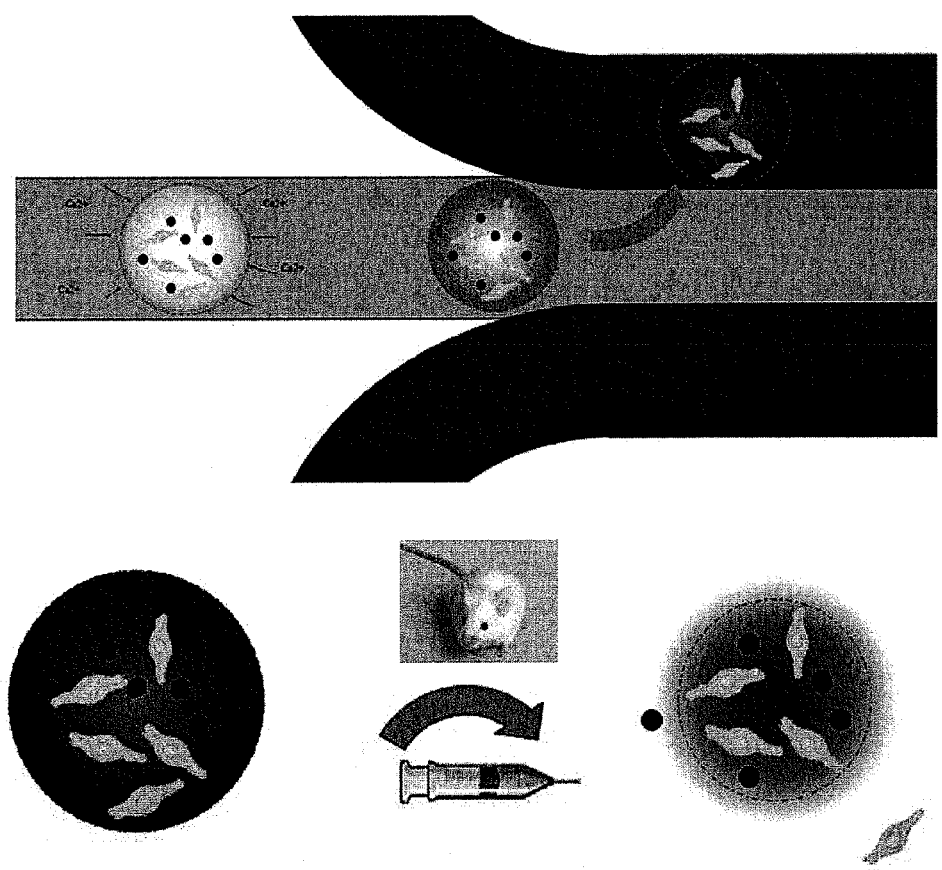
FIG. 5 is a schematic illustration of a stabilization channel and process according to an embodiment of the current invention.
Figure 6:
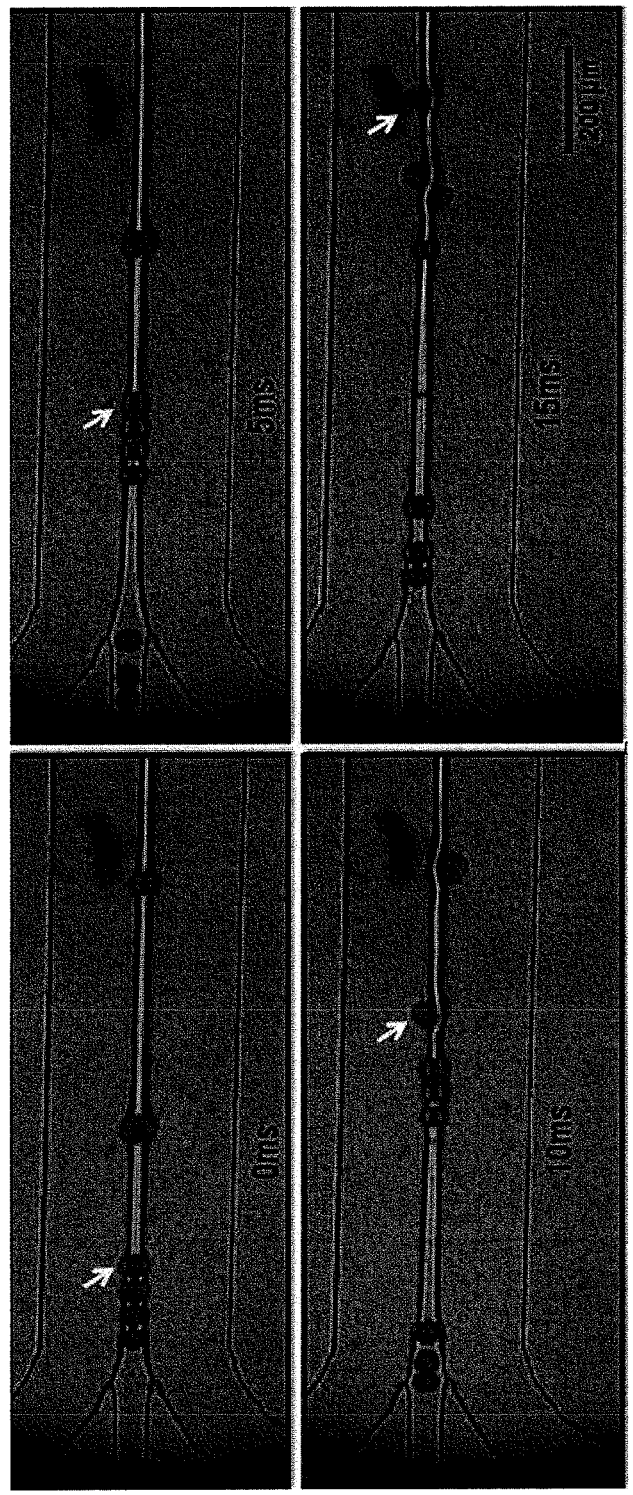
FIG. 6 shows a time sequence of a stabilization channel for beads produced according to an embodiment of the current invention. In this example, clusters of gel beads enter the stabilization channels, with the leading bead indicated with a white arrow for clarity. The central calcified oleic acid stream is miscible with the lateral IPA/aqueous calcium streams. Microbeads are kept in single file to prevent inadvertent inter-bead crosslinking, by constraining them hydrodynamically. They then cross into the lateral streams rapidly and are stabilized. Synthesis rate is approximately 250 Hz.

In the examples of FIGS. 1 and 2A, the stabilizing channel receives stabilizing fluid from two or more inlet channels, as is further illustrated schematically in FIG. 5. FIG. 6 shows an actual example of the production of microbeads over a time sequence.

In some embodiments, the supply channel has cross sectional dimensions for producing beads that are correspondingly at least 15 µm and less than 80 µm. In further embodiments, the supply channel has cross sectional dimensions for producing beads that are correspondingly at least 40 µm and less than 60 µm. Embodiments of the system 100 have been found to be suitable for producing microbeads that are highly uniform. For example, coefficients of variation of at least 50%, and as small as 10% have been achieved. Some embodiments have coefficients of variation of 20-30%.

In some embodiments, microbeads can be produced at each supply-channel-shearing-channel interface at a rate of at least 50 Hz and up to a rate of about 200 Hz. Suitable operating pressures, for some applications, for the valve, supply, and shearing channels are 15, 20 and 12 psi, respectively. However, the broad concepts of the current invention are not limited to this example. For example, suitable pressures depend on the viscosity of the microbead precursor material, for example the alginate solution, which in turn depends on the concentration of the alginate.

In some embodiments, the supply channel 104 defined by said microfluidic device 102 can bifurcate into a plurality of subchannels 124, each arranged to open into the shear channel 106 for producing of a plurality of microbeads in parallel from the supply channel 104. Each of the subchannels 134 has a corresponding check valve. In the example of FIG. 2A, there are five subchannels, consequently if each is producing droplets at a rate of 200 Hz, the supply channel 104 is producing droplets at a combined rate of 1 kHz.

In some embodiments, the microbead precursor material includes alginate and the carrier fluid includes calcified oleic acid. In some embodiments, the microbead precursor material includes alginate, the carrier fluid includes calcified oleic acid, and the stabilizing fluid includes an isopropyl alcohol and calcium chloride mixture. The microbead precursor material, the carrier fluid and the stabilizing fluid are not limited to these particular examples. The microbead precursor material can include monomers for a polymerization reaction and the carrier material can include crosslinkers to stabilize the droplets during formation of microbeads. In some embodiments, the microbead precursor material can include at least one of a diagnostic agent, a therapeutic agent, or a living organism. The diagnostic agent can be at least one of a fluorophore, an x-ray tracer, a magnetic material, acoustic reflector, or a radioactive material, for example. (Also, see Brad P. Barnett, et al., Nature Protocols, Vol. 6, No. 8 (2011) 1142-1151, the entire contents of which are incorporated herein by reference.) In some embodiments, the microbead precursor material can include, but is not limited to, at least one of alginate, barium sulfate, bismuth sulfate, iron oxide particles, paramagnetic chelates, perfluorocarbons, and cells. In some embodiments, small molecules and/or large molecules can be included in the microbead precursor material, such as, but not limited to, pharmaceuticals, DNA, RNA and proteins.

In operation, a bias pressure is applied to the check valve 118 by the pressure distribution system 112 through tube 128 and control channel 124. Pressure is applied to the carrier fluid in the shearing channel 106 by the pressure distribution system 112 through tube 132, but with a pressure that is less than the bias pressure. Pressure is applied to the microbead precursor material in the supply channel 104 by the pressure distribution system 112 through tube 114 with a pressure that is greater than the bias pressure in order to open the check valve 118. Droplets are then formed by shearing action of the carrier fluid in the shearing channel 106. The droplets begin to stabilize as they travel along the shearing channel 106. The droplets stabilize further into microbeads in the stabilization channel 130 until they pass into the outlet 136. The microbeads can be removed and/or further processed in a wide variety of ways from the outlet 136.

EXAMPLES

We have fabricated a microfluidic device as described (FIGS. 2A-2C). The device has four inlets (subchannels), for a calcified oleic acid carrier phase, an alginate solution, a valve control inlet for pressurizing a PDMS membrane, and a 2:1 IPA/aqueous calcium chloride stabilization phase containing ~7% wt calcium (FIG. 2A). Each of these inlets was connected to a pressure source, which is controlled by a precision regulator (Porter Instruments). An 8 mm-diameter hole is punched at the outlet to collect the fabricated beads, which are manually pipetted out. When pressurized, the PDMS membrane forms a near-perfect seal against the glass coverslip bottom. The inlets are then driven by pressure in this order to prevent clogging along the channels: i) calcified oleic acid, ii) the stabilization phase, and iii) the alginate solution. The pressures should be such that $P_{alginate} > P_{valve} > P_{oil}$.

The high-pressure alginate stream pries open the PDMS membrane-glass seal, and gets side-sheared by the oleic acid into micro-droplets (FIG. 2B). The low concentration calcium in the calcified oleic acid then diffuses slowly across the oil-water interface, and partially crosslinks the droplets into gel microbeads. The gel at this point is stable enough to not coalesce, but without further crosslinking, tends to aggregate when left standing in contact (probably from cross-diffusion of calcium and alginate). Two streams of IPA/aqueous calcium chloride solution then flank the oleic acid carrying the nascent microbeads, which "jump" into the side streams due to surface tension (FIGS. 5 and 6). The pressure of the stabilization solution is not critical, though it should be adjusted such that the oleic acid stream is slightly focused by the lateral streams to ensure that the beads remain in single-file until they are fully crosslinked to minimize chances of aggregation. The microbeads are heavily crosslinked as the IPA/water/oleic acid mixture exits into the collection chamber.

Cells, barium sulfate crystals, gadopentetate dimeglumine, perfluoro-octylbromide emulsion, and superparamagnetic microparticles have all been incorporated into the alginate solution prior to injection, and encapsulated in the beads to confer various functions. Protamine sulfate and chitosan, on the other hand, have been coated onto the microbeads by co-solubilizing them in the IPA/water stabilizing solution with calcium chloride. The beads generated in this manner can be stored for at least 4 months without any apparent changes to the morphology.

The bead generation using this method can easily reach 250 Hz per nozzle (FIG. 2C, FIG. 6). In this example embodiment, a total frequency of 1 kHz can be routinely achieved. Beads generated range from 15 to 50 microns, with other sizes possible through variations of nozzle geometry. The coefficient of variation (standard deviation divided by mean diameter) of the bead sizes, as determined by image analysis is ~20%.

High IPA concentration is clearly non-optimal for cell culture in microbeads. Therefore, a flow fractionation method is currently being developed to extract the beads from the IPA solution as soon as crosslinking is complete.

Figures 7A, 7B, 7C:
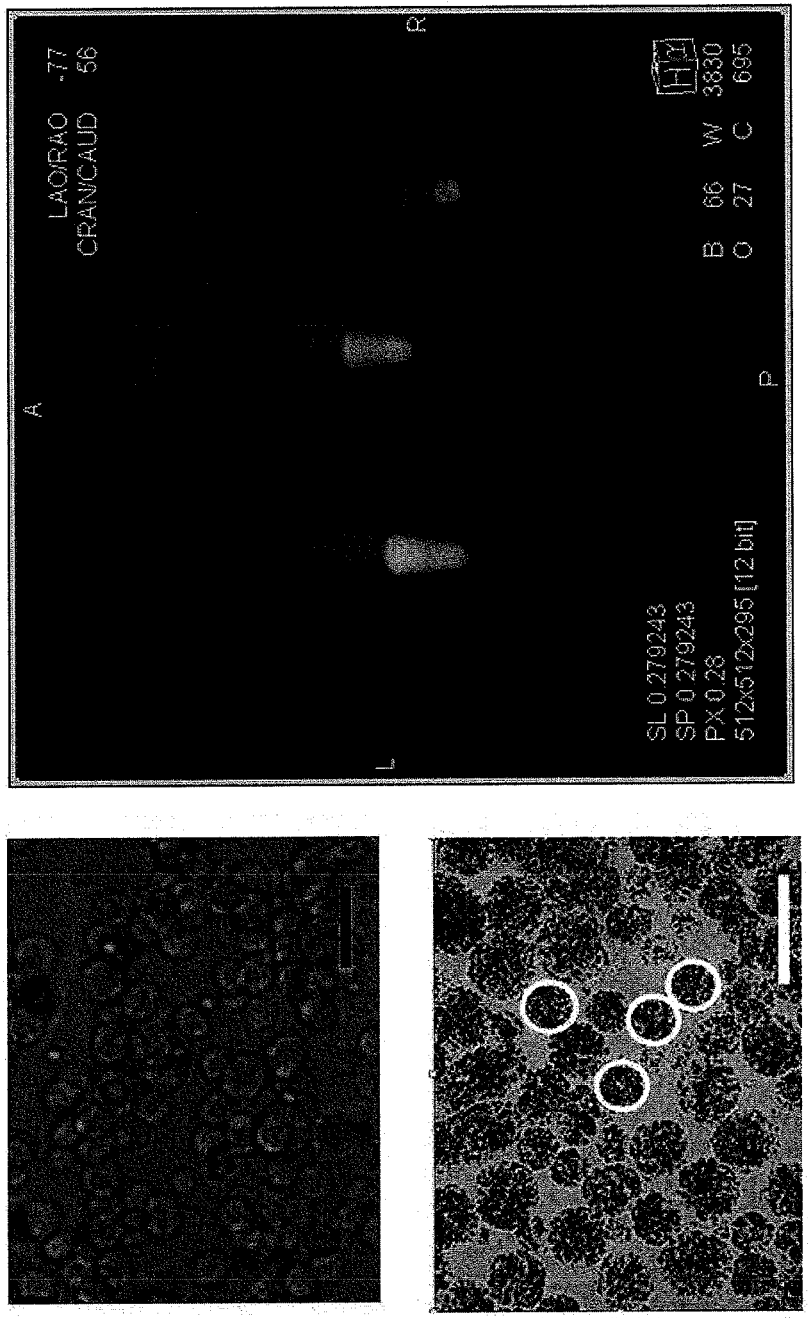
FIGS. 7A-7C show examples of beads produced according to an embodiment of the current invention.
Figure 8:
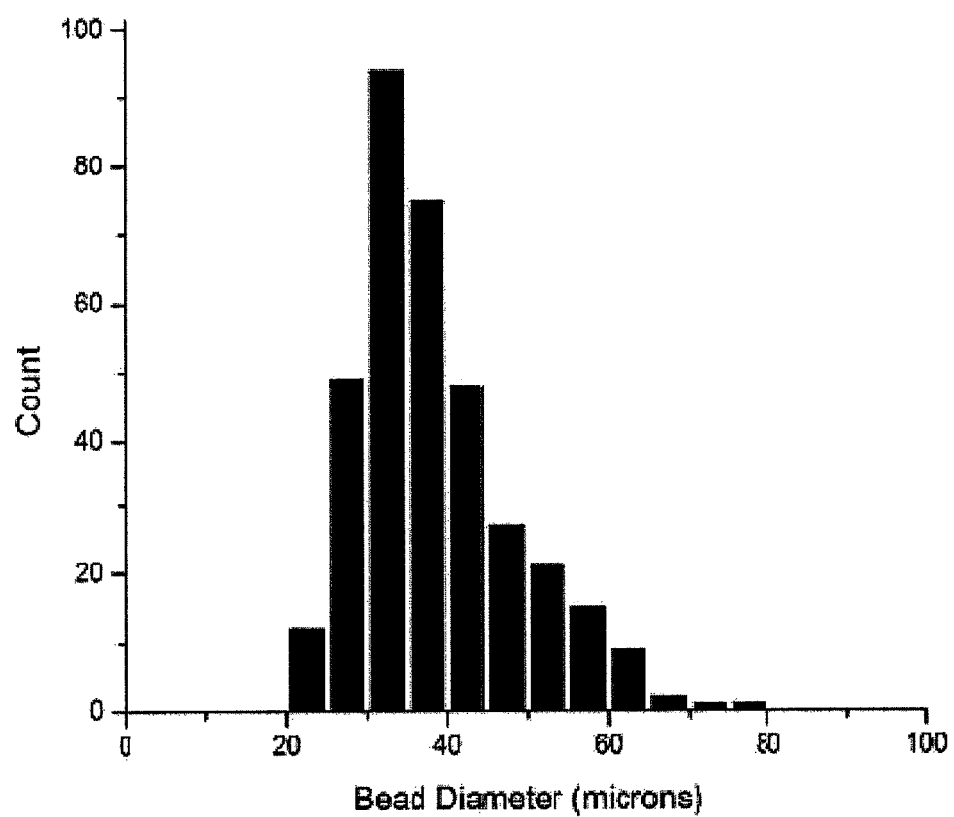
FIG. 8 shows an example of size distribution of microbeads produced according to an embodiment of the current invention.

With devices according to some embodiments of the current invention, we have been able to generate large quantities of fairly monodisperse beads, and also introduced microns-sized particles into the beads (FIGS. 7A-7C). In particular, beads with barium sulfate encapsulated were fabricated at a quantity large enough to be visible on a clinical X-ray CT scanner, thus indicating our ability to bridge the microfluidics-macroworld gap.

Materials and Methods i) Device Fabrication. A two-layer microfluidic device was fabricated as previously described (Quake SR, Scherer A. From micro- to nanofabrication with soft materials. Science 2000 Nov. 24;290(5496):1536-1540). Briefly, photoresist molds (using SU-8, MicroChem and SPR 220-7, Megaposit) were fabricated on silicon wafers. A 7:1 base/curing agent polydimethylsiloxane (PDMS, Sylgard 184) was cast onto the valve control layer, while a 15:1 base/curing agent PDMS was spun at 1200 rpm onto a wafer containing the fluidic layer. The two were partially cured and bonded together to form the PDMS membrane valves. Inlet holes were punched using a sharpened 23 G needle, while the collection chamber was formed using an 8 mm biopsy punch (Uni-core). The microfluidic channels were then sealed using a glass coverslip after oxygen plasma treatment.

ii) Calcified Oleic Acid. Calcified oleic acid was prepared by mixing saturated calcium chloride in methanol with oleic acid (1:1 by volume), and leaving to stand for two days. The calcified oleic acid was taken from the bottom layer of the phase-separated mixture and diluted with oleic acid to the desired concentration. In a typical preparation the dilution factor is 10.

iii) Alginate solution. For cell encapsulation experiments, a cell suspension was spun down and the pellet was resuspended in a suitable amount of calcium-free culture medium. The various components were then mixed with a 2% sodium alginate solution in PBS, and diluted to a 1% final alginate concentration mixture using PBS. Around 10 million cells/mL should be used in the final alginate solution, since at 50 pL per bead, 1 mL will generate 20 million cells. Much lower cell concentrations will result in many empty beads that contain no cells. When barium sulfate is used, the crystals are first suspended in PBS and sonicated using a probe sonicator for 3 minutes before use. This ensures that the crystals are well dispersed. The high viscosity of the alginate solution limits the effects of gravity on the degree of dispersion of the suspended components, though it is still recommended that suspensions be prepared fresh and used within an hour.

iv) Stabilization Solution. An IPA-aqueous calcium chloride mixture (2:1 by volume) was prepared for stabilization of the beads post generation. Polycations such as protamine sulfate and chitosan can also be added.

v) Device Operation. The various prepared solution were loaded into tygon tubings and injected into the microfluidics device using a regulated pressure source (compressed air) in the following order: i) Valve control; ii) calcified oleic acid; iii) stabilization solution; and iv) alginate with various payloads. That sequence prevents backflow of calcified oleic acid into the alginate channels, which can cause significant clogging. Further, the typical pressures used were $P_{alginate}$=20 psi, $P_{valve}$=15 psi, $P_{oil}$=12 psi and $P_{stabilization}$=20 psi. Fabricated beads were collected into PCR tubes for storage by pipetting.

vi) X-Ray Computed Tomography. Multiplanar reformats were obtained on standard reconstructed cone beam CT images (DynaCT, Siemens Axiom Artis dFA) acquired using the standard head preset (20 s acquisition; 48 cm field-of-view; 70 kV; 45 mAs; 200 degree rotation, 0.5 degree angle increment; and 120 cm SID). The microbeads appear as a hyperintense pellet in the bottom of the microcentrifugation tubes on the c-arm CTs.

Some embodiments of the current invention can provide one or more of the following:

Robust System: The use of low-concentration crosslinkers allow beads to be generated at high frequency and in close proximity without coalescence. The check valve membrane system prevents inadvertent crosslinking at the nozzle which can result in clogging.

Ease of Scaling Up: Robustness of system allows the use of multiple nozzles on a single device and/or multiple devices running in parallel without excessive fine-tuning.

High-Speed Generation: Ability to prevent coalescence and ease of scaling up generation makes high-speed generation possible. Currently, fabrication at 1 kilohertz on a single device is possible.

Highly Uniform Small Beads: Bead morphology controlled primarily by nozzle geometry, and secondarily by the pressure settings, both of which can be easily manipulated, thereby creating highly uniform beads. Small sizes of the microbeads allow the delivery by means of clinically-used catheters.

Extremely Stable: Beads stabilized with the system can remain stable for months when stored in the appropriate conditions without any changes in morphology.

Ease of Surface Modification: Different polymers and biological molecules can be dissolved in the stabilization solution, and they will coat the microbeads when these are introduced into said solution.

Ease of Incorporation of Different Materials: Different materials can be incorporated in the bead matrix simply by mixing prior to injection into the microfluidic device.

Some applications can include, but are not limited to, a platform for generation of a variety of microbeads, with co-encapsulation of cells and biologics for various applications. Pre-formed beads can be used as a culture platform for tissue engineering applications. Beads with co-encapsulated imaging contrast agents and magnetic particles can be manipulated to provide imaging information on specific regions of the body using external magnets or X-ray sources to localize the beads. Beads for embolic therapy can be made at high rate with uniform bead size and imaging visibility. Magnetic particle beads can be used for magnetic hyperthermia treatment using low alternating magnetic fields.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for producing microbeads, comprising:
   a microfluidic device defining a supply channel and a shearing channel;
   a microbead precursor material disposed in said supply channel;
   a carrier fluid disposed in said shearing channel; and
   a pressure distribution system fluidly connected to each of said supply channel and said shearing channel to control at least relative pressures of said microbead precursor material and said carrier fluid,
   wherein said supply channel comprises a check valve adapted to be subjected to a bias pressure that is sufficient to close said check valve to flow of microbead precursor material when a supply pressure of said microbead precursor material is below a threshold pressure and is open to flow of said microbead precursor material when said supply pressure of said microbead precursor material is greater than said threshold pressure,
   wherein an end of said supply channel opens into said shearing channel such that said microbead precursor material is sheared into droplets by said carrier fluid flowing through said shearing channel,
   wherein a pressure of said carrier fluid is less than said bias pressure,
   wherein said microbead precursor material and said carrier fluid are substantially immiscible,
   wherein said microfluidic device further defines a control channel operatively connected to said check valve, said system for producing microbeads further comprising a control fluid disposed in said control channel,
   wherein said pressure distribution system is further fluidly connected to said control channel to control said bias pressure, and
   wherein said microfluidic device further defines a stabilizing channel, said system for producing microbeads further comprising stabilizing fluid disposed in said stabilizing channel, said stabilizing fluid being at least partially miscible with said microbead precursor material and said carrier material,
   wherein said stabilizing channel is arranged such that said stabilizing fluid interfaces with said carrier fluid to further stabilize said droplets to form said microbeads.

2. A system for producing microbeads according to claim 1, wherein said supply channel is configured to produce beads that have an average diameter of at least 15 μm and less than 80 μm.

3. A system for producing microbeads according to claim 1, wherein said supply channel is configured to produce beads that have an average diameter of at least 40 μm and less than 60 μm.

4. A system for producing microbeads comprising:
   a microfluidic device defining a supply channel and a shearing channel;
   a microbead precursor material disposed in said supply channel;
   a carrier fluid disposed in said shearing channel; and
   a pressure distribution system fluidly connected to each of said supply channel and said shearing channel to control at least relative pressures of said microbead precursor material and said carrier fluid,
   wherein said supply channel comprises a check valve adapted to be subjected to a bias pressure that is sufficient to close said check valve to flow of microbead precursor material when a supply pressure of said microbead precursor material is below a threshold pressure and is open to flow of said microbead precursor material when said supply pressure of said microbead precursor material is greater than said threshold pressure,
   wherein an end of said supply channel opens into said shearing channel such that said microbead precursor material is sheared into droplets by said carrier fluid flowing through said shearing channel,
   wherein a pressure of said carrier fluid is less than said bias pressure, and wherein said microbead precursor material and said carrier fluid are substantially immiscible, and
   wherein said system for producing microbeads is configured to produce microbeads from said supply channel at a rate of at least 200 Hz.

5. A system for producing microbeads according to claim 1, wherein said supply channel defined by said microfluidic device bifurcates into a plurality of subchannels, each arranged to open into said shear channel for producing of a plurality of microbeads in parallel from said supply channel, and
   wherein each of said subchannels has a corresponding check valve.

6. A system for producing microbeads according to claim 1, wherein said microbead precursor material comprises alginate and said carrier fluid comprises calcified oleic acid.

7. A system for producing microbeads according to claim 1, wherein said microbead precursor material comprises alginate, said carrier fluid comprises calcified oleic acid, said stabilizing fluid comprises an isopropyl alcohol and calcium chloride mixture.

8. A system for producing microbeads according to claim 1, wherein said microbead precursor material comprises at least one of a diagnostic agent, or a therapeutic agent.

9. A system for producing microbeads according to claim 8, wherein said diagnostic agent is at least one of a fluorophore, an x-ray tracer, a magnetic material or a radioactive material.

10. A system for producing microbeads according to claim 4, wherein said microbead precursor material comprises monomers for a polymerization reaction and said carrier material comprises crosslinkers to stabilize said droplets during formation of microbeads.

11. A system for producing microbeads according to claim 4, wherein said supply channel is configured to produce beads that have an average diameter of at least 15 μm and less than 80 μm.

12. A system for producing microbeads according to claim 4, wherein said supply channel is configured to produce beads that have an average diameter of at least 40 μm and less than 60 μm.

13. A system for producing microbeads according to claim 4, wherein said supply channel defined by said microfluidic device bifurcates into a plurality of subchannels, each arranged to open into said shear channel for producing of a plurality of microbeads in parallel from said supply channel, and wherein each of said subchannels has a corresponding check valve.

14. A system for producing microbeads according to claim 4, wherein said microbead precursor material comprises alginate and said carrier fluid comprises calcified oleic acid.

15. A system for producing microbeads according to claim 4, wherein said microbead precursor material comprises at least one of a diagnostic agent, or a therapeutic agent.

16. A system for producing microbeads according to claim 15, wherein said diagnostic agent is at least one of a fluorophore, an x-ray tracer, a magnetic material or a radioactive material.

17. A system for producing microbeads according to claim 1, wherein said microbead precursor material comprises monomers for a polymerization reaction and said carrier material comprises crosslinkers to stabilize said droplets during formation of microbeads.

* * * * *